United States Patent
Faour et al.

(10) Patent No.: US 6,569,456 B2
(45) Date of Patent: May 27, 2003

(54) OSMOTIC DEVICE CONTAINING DILTIAZEM AND AN ACE INHIBITOR OR DIURETIC

(75) Inventors: Joaquina Faour, Buenos Aires (AR); Juan A. Vergez, Buenos Aires (AR)

(73) Assignee: Osmotica Corp., Tortola (VG)

( * ) Notice: Subject to any disclaimer, the term of this patent is extended or adjusted under 35 U.S.C. 154(b) by 0 days.

(21) Appl. No.: 09/755,371

(22) Filed: Jan. 5, 2001

(65) Prior Publication Data
US 2002/0006430 A1 Jan. 17, 2002

Related U.S. Application Data
(60) Provisional application No. 60/176,174, filed on Jan. 13, 2000.

(51) Int. Cl.[7] .............................. A61K 9/22; A61K 9/30; A61K 9/36

(52) U.S. Cl. ..................... 424/473; 424/468; 424/474; 424/475; 424/480; 514/772.3; 514/781

(58) Field of Search ................................. 424/468, 478, 424/473, 474, 475, 480, 482

(56) References Cited

U.S. PATENT DOCUMENTS

| | | |
|---|---|---|
| 4,264,611 A | 4/1981 | Berntsson et al. |
| 4,472,380 A | 9/1984 | Harris et al. |
| 4,703,038 A | 10/1987 | Garthoff et al. |
| 4,983,598 A | 1/1991 | Cavero et al. |
| 5,037,821 A | 8/1991 | Horovitz |
| 5,508,044 A * | 4/1996 | Buxton et al. ............... 424/495 |
| 6,004,582 A | 12/1999 | Faour et al. |
| 6,146,662 A | 11/2000 | Jao et al. |

OTHER PUBLICATIONS

Electronic Orange Book Online Excerpt, TECZEM®.
Hricik, D.E. et al., Evaluation of enalapril/diltiazem ER in hypertensive patients with coexisting renal dysfunction. Enalapril/Diltiazem ER in Hypertensive Renal Disease Group., J. Hum Hypertens, Nov. 1996, 10 (11): 769–774.
Los, L.E. et al., Gender differences in toxicokinetics, liver metabolism, and plasma esterase activity: observation from a chronic (27–week) toxicity study of enalapril/diltiazem combination in rats, Drug Metab Dispos, Jan. 1996, 24 (1): 28–33.
Ferme, I. et al., Comparative study on monotherapy with sustained–release diltiazem 300 mg and enalapril 20 mg in mild to moderate arterial hypertension., J Cardiovasc Pharmacol, 1990, 16 Suppl 1: S46–50.
Applegate, W.B. et al., Evaluation of blood pressure response to the combination of enalapril (single dose) and diltiazem ER (four different doses) in systemic hypertension., Am J Cardiol, Jul. 1996; 78 (1): 51–55.

(List continued on next page.)

Primary Examiner—James M. Spear
(74) Attorney, Agent, or Firm—Rick Matos; Innovar, L.L.C.

(57) ABSTRACT

The present invention provides an osmotic device containing controlled release diltiazem in the core in combination with a rapid release ACE inhibitor, or diuretic, in an external coat. The delivery device of the invention can also be a chronotherapeutic osmotic device that provides a delayed and controlled release of diltiazem and a delay and rapid release of an ACE inhibitor or diuretic. A wide range of ACE inhibitors or diuretics can be used in this device. Particular embodiments of the invention provide osmotic devices having predetermined release profiles. One specific embodiment of the osmotic device includes an external coat that has been spray coated rather than compression coated onto the device. The device with spray coated external core is smaller and easier to swallow than the similar device having a compression coated external coat. The device is useful for the treatment of blood pressure or hypertension related disorders.

59 Claims, 4 Drawing Sheets

OTHER PUBLICATIONS

Weir, R.J. et al., A multicentre study to compare the therapeutic efficacy of sustained–release diltiazem and enalapril in the treatment of patients with mild to moderate hypertension., Br J Clin Pract, Nov.–Dec. 1994; 48 (6): 287–292.

Zannad, F. et al., Antihypertensive efficacy and tolerability of diltiazem and enalapril, alone or in combination. DESG. Diltiazem Enalapril Study Group., Presse Med, Oct. 1, 1994; 23 (29): 1335–1338.

Chrysant, S.G. et al., Clinical utility of long–term enalapril/diltiazem ER in stage 3-4 essential hypertension. Longterm use of enalapril/diltiazem ER in stage 3-4 hypertension group., J Clin Pharmacol, Sep. 1997; 37 (9): 810–5.

Gavras, H. et al., Evaluation of enalapril combined with diltiazem ER in patients with stage 3-4 essential hypertension., Clin Exp Hypertens, Jan. 1998; 20 (1): 41–52.

Cushman, W.C. et al., Comparison of the fixed combination of enalapril/diltiazem ER and their monotherapies in stage 1 to 3 essential hypertension., Am J Hypertens, Jan. 1998; 11 (1 Pt 1): 23–30.

Applegate, W. et al., Long–term effectiveness of enalapril plus extended–release diltiazem in essential hypertension., Pharmacotherapy, Jan.–Feb. 1997; 17 (1): 107–112.

* cited by examiner

OSMOTIC DEVICE CONTAINING DILTIAZEM AND AN ACE INHIBITOR OR DIURETIC

CROSS-REFERENCE TO EARLIER FILED APPLICATION

This application claims the benefit of Provisional Application No. 60/176,174 filed Jan. 13, 2000.

FIELD OF THE INVENTION

This invention pertains to an osmotic device containing diltiazem and an angiotensin converting enzyme (ACE) inhibitor. More particularly, it pertains to an osmotic device tablet which provides a controlled release of diltiazem and a rapid or immediate release of an ACE inhibitor diuretic compound.

BACKGROUND OF THE INVENTION

ACE inhibitors, diuretics and calcium channel blockers are three types of antihypertensive agents used either as monotherapy or in combination to regulate blood pressure in the treatment of hypertension. The efficacy of ACE inhibitors is related to the initial level of plasma angiotensin II (Ang II) or plasma renin activity. However, patients with low plasma renin activity also experience a fall in blood pressure during ACE inhibitor therapy. In contrast to diuretics, diltiazem does not have adverse metabolic effects on electrolytes, carbohydrate metabolism and lipid metabolism. Diltiazem is particularly indicated in patients with hypertension and concurrent angina pectoris, diabetes, hyperlipidemias and chronic renal disease.

The commercially available product TILAZEM™ (Parke-Davis) is a sustained release form of diltiazem. It has been reported to provide an adequate therapeutic benefit but causes unwanted side effects.

While each type of drug has demonstrated efficacy in the clinic, combinations of a calcium channel blocker with an ACE inhibitor or a diuretic are more effective, i.e., the drugs typically exhibit additive, if not synergistic, therapeutic benefits. Clinical trials have documented the augmentation of blood pressure reduction when these agents are combined as compared to the individual agents. In addition, clinical results have shown that combination therapy may be effective even in situations where each agent alone is ineffective.

The calcium channel blocker and ACE inhibitor can be administered in single or multiple dosage forms. Single dosage unit combination tablet and capsule dosage forms containing a combination of diltiazem (DZ) with an ACE inhibitor, such as enalapril (ENA), captopril (CAP), or lisinopril (LIS), are known. These combination dosage forms generally provide a rapid release of the ACE inhibitor and a controlled release of DZ. These tablets are generally made for once- or twice-daily administration.

The commercial product TECZEM™ is a combination product providing an extended release form of diltiazem and an immediate release form of enalapril. This combination therapy has; been shown to be more effective than either agent alone in treating patients that do not respond well to either agent individually. The product has been associated with side effects such as dizziness, headache, cough, rash, asthenia, fatigue, impotence, edema/swelling, among other adverse events. These side effects usually begin shortly after administration of a unit dose and may continue upon chronic administration depending upon a physician's ability to titrate the dose for the patient. The discomforts of cough, dizziness and headache in a patient generally cause insomnia in a patient.

Osmotic devices and other tablet formulations are known for their ability to provide a controlled release of a wide range of drugs. Such osmotic devices and other tablet formulations are disclosed in U.S. Pat. No. 4,968,507 to Zentner et al., U.S. Pat. No. 4,014,334 to Theeuwes et al., U.S. Pat. No. 4,576,604 to Guittard et al., Argentina Patent No. 234,493, U.S. Patent No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770 and Argentina Patent No. 199,301, the entire disclosures of which are hereby incorporated by reference. Osmotic devices containing diltiazem, such as the controlled porosity osmotic pump disclosed in U.S. Pat. No. 4,880,631 to Haslam et al., are also known.

While conventional sustained release dosage forms, such as described above, are effective, osmotic devices such as those described by Faour et al. (U.S. Pat. No. 6,004,582), Harris et al. (U.S. Pat. No. 4,472,380), and Cavero et al., the entire disclosures of which are hereby incorporated by reference, are particularly advantageous for delivering two different dosage forms from a single osmotic device tablet. Faour et al., Harris et al., and Cavero et al., however, do not disclose the specific combination osmotic device formulations claimed herein. Moreover, Faour et al., Harris et al., and Cavero et al. do not disclose osmotic devices that provide the specific plasma profiles or release profiles for the various different combinations claimed herein, nor osmotic devices having a drug containing external coat that has been spray coated rather than compression coated onto the device.

Mammals suffering from blood pressure related disorders generally require administration of specific amounts of a calcium channel blocker and/or ACE inhibitor at night while resting when the risk of suffering a cardiovascular event is highest. Accordingly, people suffering from these disorders generally stay up late or wake up in the middle of the night to take their medication. In addition, commercially available products do not currently address the issue of timed administration of the calcium channel blocker and/or ACE inhibitor.

Chronotherapy refers to the timed administration of therapeutically effective agents. For solid dosage forms, chronotherapy is achieved by the use of delayed release coatings to delay the release of one or more drugs until an approximately predetermined time period. It would be useful to develop a chronotherapeutic dosage form containing diltiazem and an ACE inhibitor. The prior art does not disclose a chronotherapeutic osmotic device having a delayed release of both the diltiazem and the ACE inhibitor or diuretic agent, wherein the release of diltiazem is controlled and the release of the ACE inhibitor is rapidly.

SUMMARY OF THE INVENTION

In one aspect, the present invention provides a chronotherapeutic osmotic device comprising:

a core comprising a therapeutically effective amount of diltiazem and at least one osmotic agent or osmopolymer, wherein the core provides a controlled release of diltiazem;

a semipermeable membrane surrounding the core and having a passageway there through; and an external coat comprising a therapeutically effective amount of an angiotensin converting enzyme inhibitor or diuretic, wherein the external coat provides a rapid release of the ACE inhibitor or diuretic; wherein:

at least 80% of the DZ is released within 20 hours, and at least 45% of the ACE inhibitor is released within 40 minutes, or at least 75% of the diuretic is released within about 40 minutes, after exposure of the osmotic device to an aqueous solution; and initial release of the DZ and optionally the ACE inhibitor or diuretic is delayed for a period of at least about 1.5 hours.

In some specific embodiments, the ACE inhibitor is selected from the group consisting of enalapril (ENA), captopril (CAP), lisinopril (LIS), benazepril (BEN), enalaprilat (ENAP), espirapril (ESP), fosinopril (FOS), moexipril (MXP), quinapril (QNA), ramipril (RAM) perindopril, and trandolapril (TND).

In other specific embodiments, the diuretic is selected from the group consisting of high-ceiling diuretics, furosemide, bumetanide, ethacrynic acid, torsemide, muzolimide, azosemide, piretanide, tripamide, chlorothiazide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide and benzothiazide.

In still other specific embodiments, the external coat is applied by spray coating rather than by compression coating. By spray coating rather than compression coating the external coat, a thinner external coat, and therefore a smaller osmotic device, is formed.

Another aspect of the invention provides a method of treating hypertension in a mammal, the method comprising the step of administering an osmotic device which provides a controlled release of diltiazem from its core and a rapid release of an ACE inhibitor or diuretic from an external coat, wherein at least 75% of the ACE inhibitor is released within about 40 minutes, or at least 75% of the diuretic is released within about 40 minutes, and at least about 70% of the diltiazem is released within about 20 hours after administration.

In other specific embodiments, the osmotic device has: a) a diltiazem release profile similar to that shown in FIG. 1; or b) an ACE inhibitor or diuretic release profile similar to that shown in FIG. 2. In still other specific embodiments, the release of DZ and/or the ACE inhibitor or diuretic has a delayed onset of at least about 1.5 hours.

The osmotic device generally delivers the ACE inhibitor or diuretic to the upper GI tract and the diltiazem to the middle to lower GI tract.

Other features, advantages and embodiments of the invention will become apparent to those skilled in the art by the following description, accompanying examples.

BRIEF DESCRIPTION OF THE DRAWINGS

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Diltiazem, diuretics and ACE inhibitors are available from a large number of commercial sources. The invention provides for the administration of diltiazem and ACE inhibitors or diuretics in their free base, free acid, racemic, optically pure, diastereomeric and/or pharmaceutically acceptable salt forms.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of the DZ or ACE inhibitor. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, gluitamic, benzoic, salicylic, sulfanilic, 2-acetoxybenzoic, fumaric, toluenesulfonic, melhanesulfonic, ethane disulfonic, oxalic, isethionic, and the like. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Figure 1:
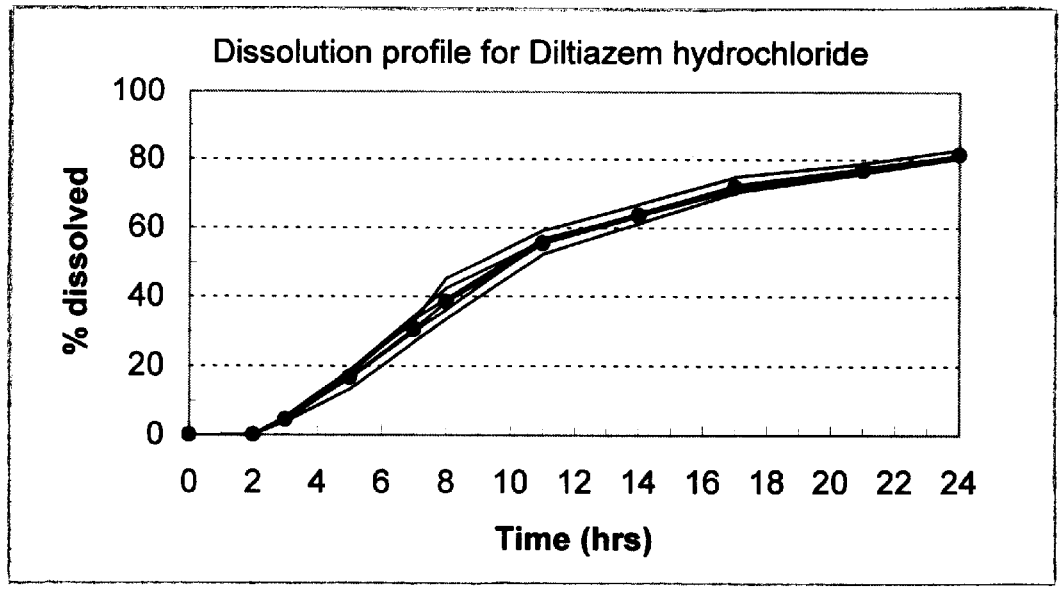
FIG. 1 depicts an in vitro release profile for diltiazem from the exemplary formulation of Example 1.

FIG. 1 depicts various diltiazem in vitro release profiles for the osmotic device tablets described in Example 1, the TECIDE formulation. The release profile for the core of each osmotic device generally resembles a pseudo-third order or third-order release profile, wherein the profile reflects the delay prior to initial release of the drug from the core. The release profile of the osmotic device of the invention can vary from that shown in FIG. 1 according to the materials used to form the core and the semipermeable covering the core. For example, the release profile can be influenced by the amount of diltiazem used to form the core, the amount of pharmaceutically acceptable excipient used to form the core, the type of pharmaceutically acceptable excipient used to form the core, and the amount or type of any other materials used to form the core such as osmotically effective solutes, osmotic agents, osmopolymers, or osmagents. The release profile can also be influenced by the material used to form the semipermeable membrane covering the core or by the material used to form any coating on the semipermeable membrane. The osmotic device of the invention can have a release profile that generally resembles a pseudo-first order, a first order, a pseudo-second order, or a second order release profile.

As shown in FIG. 1, the TEC1DE formulation exhibits an approximately 3-hour delayed onset in the release of DZ followed by a 22-hour or greater controlled release of DZ. By delayed onset is meant that no more than about 5% by wt. or 10% by wt. of the charge of indicated drug is released within the indicated delay period. The diltiazem release profile of this exemplary formulation is generally described as follows:

| Time (h) | Maximum Percent Released | Minimum Percent Released |
|---|---|---|
| 0 | 0 | 0 |
| 2 | 0.3 | 0.0 |
| 3 | 5.4 | 4.1 |
| 5 | 18.8 | 13.3 |
| 7 | 34.3 | 26.4 |
| 8 | 45.3 | 33.4 |
| 11 | 59.3 | 52.0 |
| 14 | 67.1 | 61.0 |
| 17 | 74.9 | 70.1 |
| 21 | 78.8 | 75.8 |
| 24 | 83.1 | 80.5 |

The diltiazem release profile of Example 1 can also be described as follows:

| Time (h) | Released (%) | STD (%) |
|---|---|---|
| 0 | 0 | 0 |
| 2 | 0.1 | 0.1 |
| 3 | 4.5 | 0.5 |
| 5 | 16.7 | 2.2 |
| 7 | 30.6 | 3.4 |
| 8 | 38.3 | 4.9 |
| 11 | 55.5 | 2.8 |
| 14 | 63.6 | 2.2 |
| 17 | 71.8 | 1.7 |
| 21 | 76.8 | 1.1 |
| 24 | ≧81.25 | 1.0 |

Figure 2:
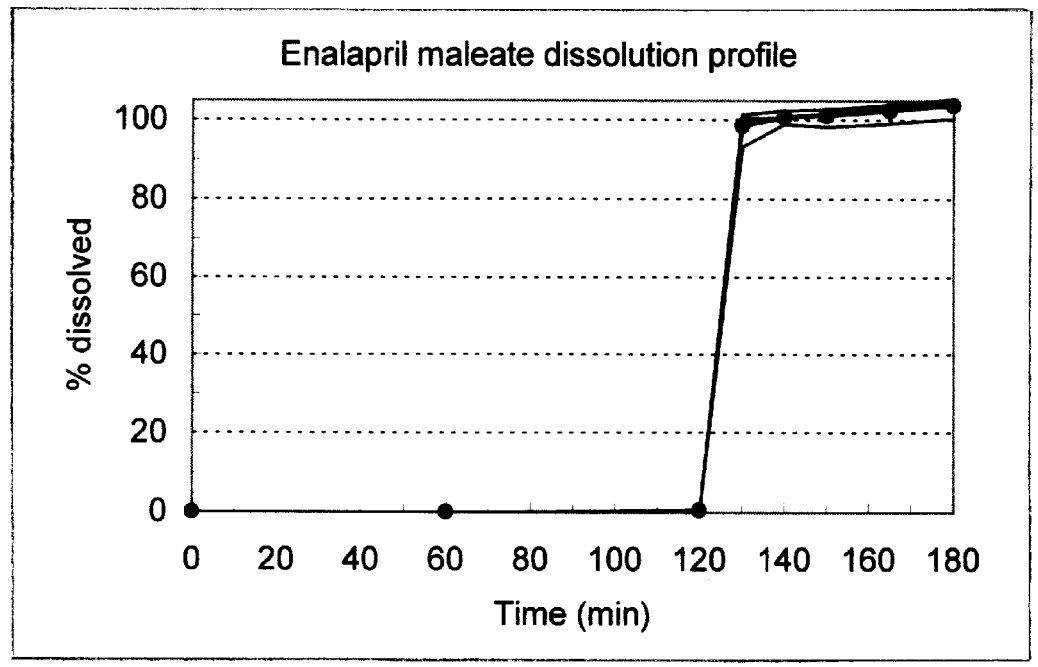
FIG. 2 depicts an in vitro release profile for enalapril from the exemplary formulation of Example 1.

FIG. 2 depicts various enalapril in vitro release profiles for the osmotic device tablets described in Example 1. The release profile for each osmotic device formed in accordance with Example 1, wherein an external coat contains either an angiotensin converting enzyme inhibitor (ACE inhibitor) or a diuretic generally resembles a pseudo-third order or third-order release profile, wherein the profile reflects the delay prior to the onset of rapid release of the drug from the coating. The enalapril release profile of the osmotic device of the invention may vary from that shown in FIG. 2 according to the materials and/or methods used to form the coating. For example, the release profile can be influenced by whether an ACE inhibitor or a diuretic is the active agent contained in the external coat, by the amount of active agent in the coat, by the amount or type of any other materials used to form the coat, or by the method used to form the coat, e.g., spray coating or compression coating. The osmotic device of the invention can have a release profile that generally resembles a pseudo-first order, a first order, a pseudo-second order, or a second order release profile.

As shown in FIG. 2, the TEC1DE formulation provides a 2-hour delayed onset for the release of enalapril followed by a sudden, immediate or very rapid release of enalapril. The enalapril release profile of this exemplary release profile is generally described as follows:

| Time (min) | Maximum Percent Released | Minimum Percent Released |
|---|---|---|
| 0 | — | — |
| 60 | — | — |
| 120 | 0.7 | 0.3 |
| 130 | 101.5 | 93.4 |
| 140 | 102.5 | 99.0 |
| 150 | 102.8 | 98.3 |
| 165 | 104.0 | 99.2 |
| 180 | 105.5 | 100.5 |

The enalapril release profile of the formulation of Example 1 can also be characterized as follows:

| Time (min) | Amount Released (%) | STD (%) |
|---|---|---|
| 0 | 0 | — |
| 60 | 0 | — |
| 120 | 0.5 | 0.1 |
| 130 | 98.6 | 2.8 |
| 140 | 100.7 | 1.1 |
| 150 | 101.2 | 1.5 |
| 165 | 102.4 | 1.7 |
| 180 | 103.8 | 1.8 |

The chronotherapeutic osmotic device of Example 1 is intended to be taken at nighttime or any other such time as when the patient is approaching bedtime or a rest period. By taking this osmotic device, the patient will receive the therapeutic benefits as needed but will also experience a delay in the onset of associated side effects. By so doing, the patient will be able to fall asleep without interruption and before the onset of the side effects.

The release profile of diltiazem for the chronotherapeutic device of Example 1 is generally described as follows.

| Time (h) | Released (%) |
|---|---|
| 0 | 0 |
| 2 | ≦5 ± 5 |
| 3 | ≦10 ± 5 |
| 5 | 15 ± 5 |
| 7 | 30 ± 5 |
| 8 | 40 ± 5 |
| 11 | 55 ± 5 |
| 14 | 65 ± 5 |
| 17 | 75 ± 10 |
| 21 | 80 ± 10 |
| 24 | ≧80 |

Figure 7:
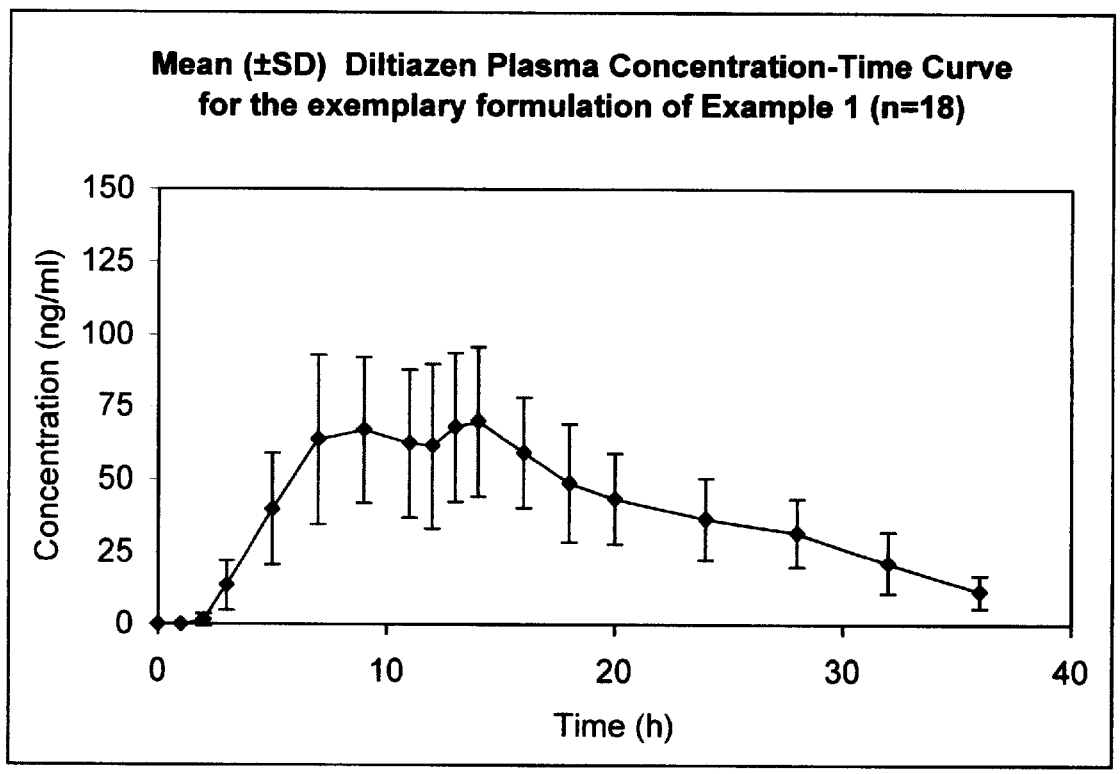
FIG. 7 depicts an in vivo diltiazem plasma profile for the exemplary formulation of Example 1.

The osmotic device of Example 1 was administered to a group of 18 humans, and the pharmacokinetic and pharmacodynamic parameters determined. FIG. 7 depicts the in vivo plasma concentration profile provided by a single dose of the osmotic device of Example 1. The data represents the mean plasma concentration of diltiazem. The observed plasma concentration profile of FIG. 7 can be described as follows:

| Time after Administration (H) | Mean Plasma Level (ng/ml) | STD (ng/ml) |
| --- | --- | --- |
| 0 | 0.0 | 0.0 |
| 1 | 0.0 | 0.0 |
| 2 | 1.6 | 2.1 |
| 3 | 13.5 | 8.7 |
| 5 | 39.8 | 19.1 |
| 7 | 63.8 | 29.3 |
| 9 | 67.2 | 25.2 |
| 11 | 62.4 | 25.4 |
| 12 | 61.5 | 28.4 |
| 13 | 68.0 | 25.7 |
| 14 | 70.0 | 25.8 |
| 16 | 59.1 | 18.9 |
| 18 | 48.8 | 20.2 |
| 20 | 43.4 | 15.5 |
| 24 | 36.5 | 14.0 |
| 28 | 31.7 | 11.6 |
| 32 | 21.4 | 10.7 |
| 36 | 11.4 | 5.7 |

The pharmacokinetic and pharmacodynamic parameters calculated from the plasma concentration profile are as follows:

| Parameter | Mean | Std Error |
| --- | --- | --- |
| $AUC_{0-t}$ (ng.h/ml) | 1419 | 465.1 |
| $AUC_{0-inf}$ (ng.h/ml) | 1548 | 507.8 |
| $K_e$ (h-1) | 0.1168 | 0.0096 |
| $C_{max}$ (ng/ml) | 81.7 | 25.7 |
| $t_{max}$ (h) | 11.5 | 2.9 |
| $T_{1/2}$ (h) | 7.7 | 4.3 |

Figure 3:
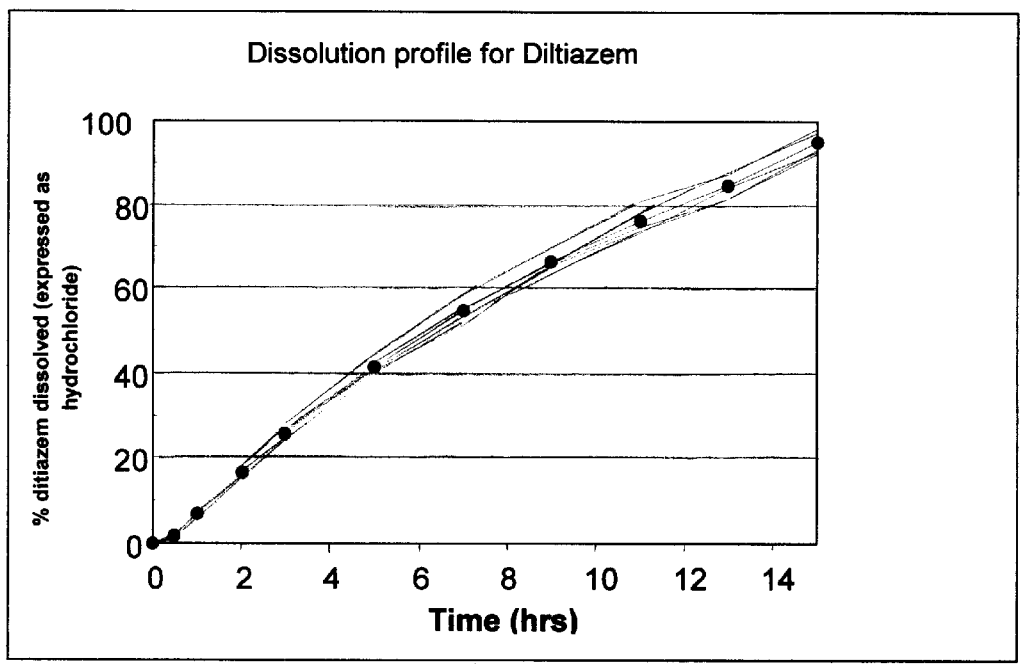
FIG. 3 depicts an in vitro release profile for diltiazem from a commercially available dosage form called TEC-ZEM™.

FIG. 3 depicts various diltiazem in vitro release profiles for the commercially available TECZEM™ formulation which is a controlled release capsule formulation. The release profile for the TECZEM™ capsule exhibits no substantial delay in the controlled release of diltiazem from the capsule.

Figure 4:
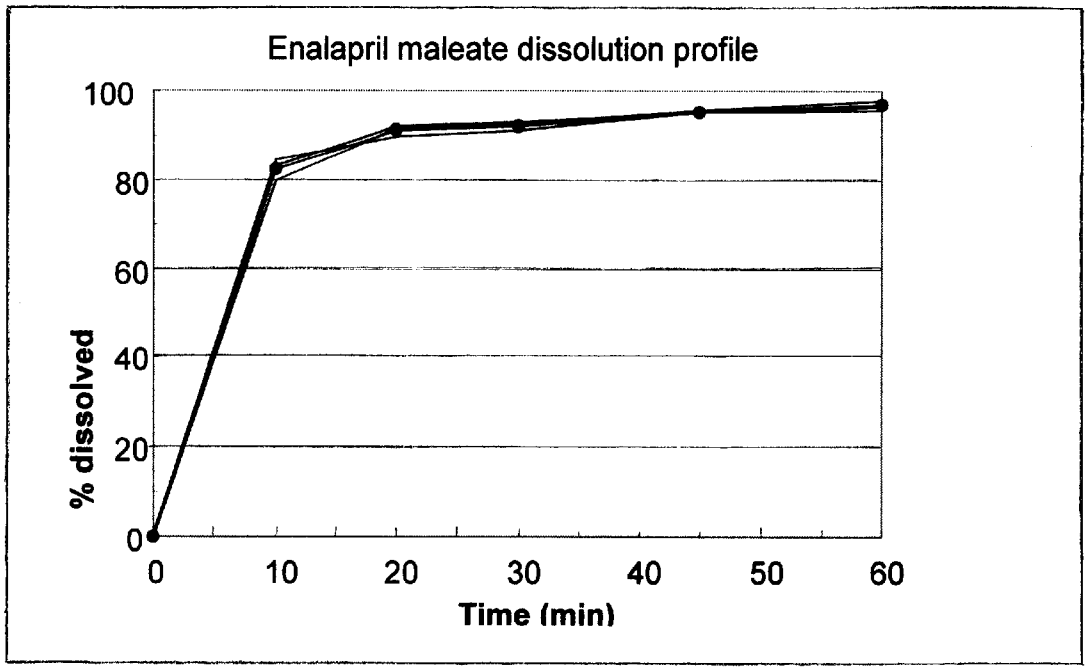
FIG. 4 depicts an in vitro release profile for enalapril from a commercially available dosage form called TECZEM™.

FIG. 4. depicts various enalapril in vitro release profiles for the commercially available TECZEM™ formulation. The enalapril release profile for the TECZEM™ product exhibits no substantial delay in the immediate release of the drug from the coating.

Since the TECZEM™ product has an immediate and rapid release of enalapril and an immediate and controlled release of diltiazem, a patient taking this dosage form will experience the rapid onset of side effects associated with this type of therapy. Therefore, the patient will experience difficulty in getting to sleep due to the dizziness, cough and headache caused by the drugs.

Figure 5:
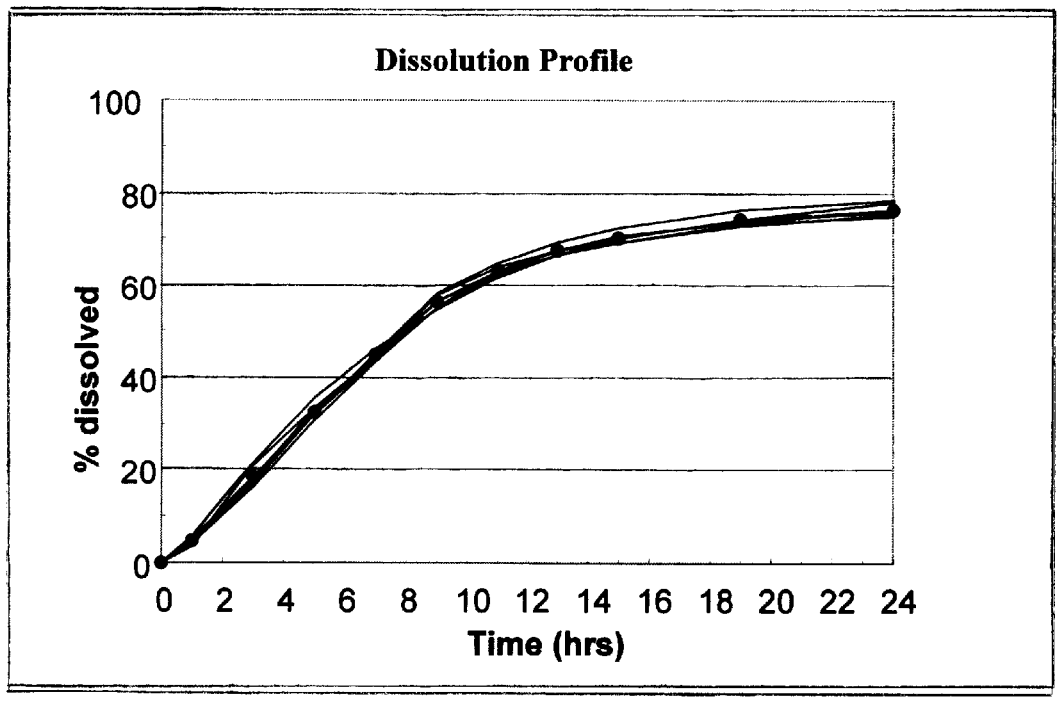
FIG. 5 depicts an in vitro release profile for diltiazem from the formulation of Example 3.

FIG. 5. depicts various diltiazem in vitro release profiles for the osmotic device tablets described in Example 3. The release profile for each osmotic device formed in accordance with Example 3 generally resembles a pseudo-third order or third-order release profile. The diltiazem release includes an approximately 1.5 to 2-hour delay period in the onset of release. The release profile of the osmotic device of the invention may vary from that shown in FIG. 5 according to the materials and/or methods used to form the coating. The diltiazem release profile depicted in FIG. 5 can be characterized as follows:

| Time (h) | Maximum Released (%) | Minimum Released (%) |
| --- | --- | --- |
| 1 | 5.6 | 3.7 |
| 3 | 21.4 | 16.4 |
| 5 | 35.5 | 30.5 |
| 7 | 45.9 | 43.5 |
| 9 | 57.9 | 54.6 |
| 11 | 64.8 | 61.9 |
| 13 | 69.2 | 66.6 |
| 15 | 72.3 | 69.4 |
| 19 | 76.1 | 72.8 |
| 24 | 78.4 | 75.1 |

The diltiazem release profile of FIG. 5 can also be characterized as follows:

| Time (h) | Amount Released (%) | STD (%) |
| --- | --- | --- |
| 1 | 4.6 | 0.7 |
| 3 | 18.6 | 2.1 |
| 5 | 32.6 | 1.7 |
| 7 | 44.6 | 0.9 |
| 9 | 55.9 | 1.4 |
| 11 | 63.1 | 1.1 |
| 13 | 67.4 | 1.0 |
| 15 | 70.4 | 1.1 |
| 19 | 74.0 | 1.2 |
| 24 | ≧76.5 | 1.4 |

The release profile of the chronotherapeutic osmotic device of Example 3 is also generally characterized as follows:

| Time (h) | Released (%) |
| --- | --- |
| 0 | 0 |
| 1 | ≦5 ± 5 |
| 3 | 20 ± 5 |
| 5 | 32 ± 5 |
| 7 | 45 ± 5 |
| 9 | 55 ± 5 |
| 11 | 65 ± 5 |
| 13 | 70 ± 5 |
| 15 | 75 ± 8 |
| 19 | 75 ± 10 |
| 24 | ≧75 |

Figure 6:
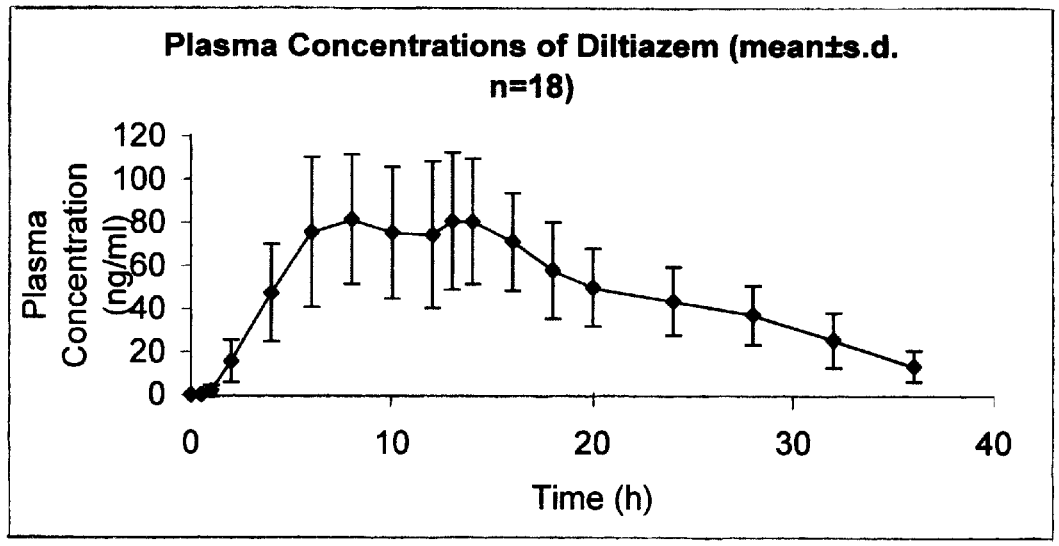
FIG. 6 depicts an in vivo diltiazem plasma profile for the exemplary formulation of Example 3.

A single dose of the osmotic device of Example 3 (FIG. 5) was administered to patients according to the procedure of Example 2. This osmotic device will generally provide a diltiazem plasma concentration profile as depicted in FIG. 6, which for a 240 mg tablet can be characterized as follows:

| Time after Administration (H) | Mean Plasma Level (ng/ml) | STD (ng/ml) |
| --- | --- | --- |
| 0 | 0.0 | 0.0 |
| 0.5 | 0.1 | 0.4 |
| 1 | 1.9 | 2.5 |
| 2 | 15.8 | 9.9 |
| 4 | 47.6 | 22.6 |
| 6 | 75.7 | 34.7 |
| 8 | 81.7 | 30.0 |
| 10 | 75.6 | 30.5 |

-continued

| Time after Administration (H) | Mean Plasma Level (ng/ml) | STD (ng/ml) |
|---|---|---|
| 12 | 74.6 | 33.9 |
| 13 | 80.9 | 31.7 |
| 14 | 80.8 | 29.1 |
| 16 | 71.4 | 22.5 |
| 18 | 58.1 | 22.4 |
| 20 | 50.2 | 18.0 |
| 24 | 43.8 | 15.9 |
| 28 | 37.5 | 13.7 |
| 32 | 25.9 | 12.7 |
| 36 | 13.8 | 7.3 |

The exemplary mean pharmacokinetic parameters for the tablets of Example 3, after administration of a single dose is summarized as follows. These pharmacokinetic data differ from the commercially available TECZEM™ (contains diltiazem and enalapril) and TILAZEM™ (contains only diltiazem) products.

| Parameter | Mean | Std Error | CV % |
|---|---|---|---|
| $AUC_{0-t}$ (ng · h/ml) | 1726.3 | 54.8 | 3.2 |
| $AUC_{0-inf}$ (ng · h/ml) | 1867.6 | 60.9 | 3.3 |
| $K_e$ (h-1) | 0.1212 | 0.0096 | 7.9 |
| $C_{max}$ (ng/ml) | 95.2 | 4.1 | 4.3 |
| $t_{max}$ (h) | 10.4 | 0.8 | 7.8 |
| $T_{½}$ (h) | 6.97 | 0.48 | 6.8 |

In a separate study, the half-life of the diltiazem was determined to be approximately 8.5±1.2 hours. The delayed release of the diltiazem causes a delay in the onset of diltiazem build-up in the plasma. Accordingly, onset of the side effects (adverse events) associated with diltiazem therapy have a delayed onset and a patient taking the medication before a rest period should not experience any difficulty in falling asleep.

Depending upon the particular combination of ingredients used to prepare the osmotic device, it may provide an expected overall diltiazem release profile resembling a pseudo-first order or first-order release profile.

According to a specific embodiment, the ACE inhibitor or diuretic has a release profile approximating the following:

| Time (min) | Released (%) |
|---|---|
| 0 | 0 |
| 60 | ≦5 |
| 120 | 5 ± 5 |
| 150 | >80 |

All of the tablet formulations of the invention will provide therapeutically effective levels of diltiazem and an ACE inhibitor or diuretic for at least a predetermined period of time. The tablets of the invention will generally provide therapeutically effective amounts of diltiazem for a period of not less than 18 hours and not more than 30 hours, preferably not less than 20 hours and not more than 28 hours, and more preferably not less than 22 hours and not more than 24 hours.

Although referred to herein as therapeutically effective levels of the named drug, the present invention provides therapeutically effective levels of one or more of the active metabolites of the named drugs. For example, where therapeutically effective amounts of diltiazem are referred to, this should be taken to mean therapeutically effective amounts of diltiazem and/or its biologically active form(s) (such as metabolites, for example), and likewise for the ACE inhibitor and diuretic.

The external coating can be an immediately dissolving coating that dissolves in the buccal cavity or a rapidly dissolving coating that dissolved in the stomach, jejunum or duodenum. The controlled release core generally begins to release diltiazem within about 2 hours after administration.

At least about 1.5 hours, 2.0 hours and generally three hours after administration, the rapid release coating will begin to rapidly release its ACE inhibitor, or diuretic, such that once release of the ACE inhibitor or diuretic begins, at least about 45% of its ACE inhibitor, or at least 75% of its diuretic, will be released in about 40 minutes.

Those of ordinary skill in the art will appreciate that the particular amounts of diltiazem, ACE inhibitor and diuretic used in the osmotic device will vary according to, among other things, the desired pharmacokinetic behavior in a mammal.

When a rapidly dissolving coat is used in the tablet formulations of the invention, the coat will generally comprise an inert and non-toxic material that is at least partially, and preferably substantially completely, soluble or erodible in an environment of use. The rapidly dissolving coat will be soluble in the buccal cavity and/or upper GI tract, such as the stomach, duodenum, jejumum or upper small intestines. Exemplary materials are disclosed in U.S. Pat. Nos. 4,576, 604 and 4,673,405, and the text Pharmaceutical Dosage Forms: Tablets Volume I, Second Edition. A. Lieberman. ed. 1989, Marcel Dekker, Inc. the relevant disclosures of which are hereby incorporated by reference. In specific embodiments, the rapidly dissolving coat will be soluble in saliva, gastric juices, or acidic fluids.

The controlled release formulations provide a delayed and sustained release of diltiazem generally include an enteric or delayed release coat that is soluble or erodible in intestinal juices, substantially pH neutral or basic fluids of fluids having a pH higher than gastric fluid, but for the most part insoluble in gastric juices or acidic fluids. A wide variety of other polymeric materials are known to possess these various solubility properties. Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HP), poly(methacrylate ethylacrylate) (1:1) copolymer (MA-EA), poly(methacrylate methylmethacrylate) (1:1) copolymer (MA-MMA), poly (methacrylate methylmethacrylate) (1:2) copolymer, Eudragit L-30-D™ (MA-EA, 1:1), Eudragit™ L-100-55™ (MA-EA, 1:1), hyciroxypropyl methylcellulose acetate succinate (HPMCAS), Coateric™ (PVAP), Aquateric™ (CAP), AQUACOAT™ (HPMCAS) and combinations thereof. The enteric coat can also comprise dissolution aids, stability modifiers, and bioabsorption enhancers.

When the delayed release coat is intended to be dissolved, eroded or become detached from the core in the colon, materials such as hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis (methacryloyloxyethyloxycarbonylamino)-azobenzene, azopolymers, enteric coated timed release system (Time Clock® from Pharmaceutical Profiles, Ltd., UK) and calcium pectinate can be used.

A specific polymeric material for use in the delayed release coat involves enteric materials that resist the action of gastric fluid avoiding permeation through the semipermeable wall while one or more of the materials in the core of the tablet are solubilized in the intestinal tract thereby allowing delivery of the diltiazem in the core by osmotic pumping in an osmotic device to begin. A material that easily adapts to this kind of requirement is a poly (vinylpyrrolidone)-vinyl acetate copolymer, such as the material supplied by BASF under its Kollidon VA64 trademark, mixed with magnesium stearate and other similar excipients. The enteric coat can also comprise povidone, which is supplied by BASF under its Kollidon K 30 trademark, and hydroxypropyl methylcellulose, which is supplied by Dow under its Methocel E-15 trademark. The materials can be prepared in solutions of having different concentrations of polymer according to the desired solution viscosity. For example, a 10% P/V aqueous solution of Kollidon K 30 has a viscosity of about 5.5–8.5 cps at 20° C., and a 2% P/V aqueous solution of Methocel E-15 has a viscosity of about 13–18 cps at 20° C.

The delayed release coat can comprise one or more materials that do not dissolve, disintegrate, or change their structural integrity in the stomach and during the period of time that the tablet resides in the stomach. Representative materials that keep their integrity in the stomach can comprise a member selected from the group consisting of (a) keratin, keratin saridarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium celllose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials known by those of ordinary skill in the art are suitable for this purpose. Exemplary materials are celllose esters, cellulose ethers and cellulose esters-ethers. However, it has been found that a semipermeable membrane consisting essentially of cellulose acetate (CA) and poly(ethylene glycol) (PEG), in particular PEG 400, are specific when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50–1% by weight of PEG, and preferably about 95% by weight of CA: about 5% by weight of PEG. The ratio can be varied to alter permeability and ultimately the release profile of the osmotic device. Other specific materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core of all the osmotic device tablet of the present invention will comprise diltiazem, at least one pharmaceutically acceptable excipient and optionally one or more other materials. Generally, the tablet formulations will comprise about 0.1–99.9% by weight of diltiazem in the uncoated tablet core. Specific ranges will vary according to the ACE inhibitor used and the intended use of the osmotic device.

When the controlled release tablet is an osmotic device, osmotically effective solutes, osmotic agents or osmagents are added. These osmagents can aid in either the suspension or dissolution of the DZ in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of DZ therefrom.

The tablets of the invention can also comprise acidifying agent, alkalizing agent, adsorbent, antioxidant, buffering agent, colorant, flavorant, sweetening agent, tablet antiadherent, tablet binder, tablet and capsule diluent, tablet direct compression excipient, tablet disintegrant, tablet glidant, tablet lubricant, tablet or capsule opaquant and/or tablet polishing agent.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium melabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherent" is intended to mean an agent that prevents the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binder" is intended to mean a substance used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to reduce friction during tablet compression. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose(e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly specific flavors are the grape and cherry flavors and citrus flavors such as orange.

The present tablets can also employ one or more commonly known surface active agents or cosolvents that improve wetting or disintegration of the tablet core or layers.

Plasticizers can also be included in the tablets to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol anc glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The tablets of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glyceridees and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of diltiazem which is sufficient to elicit the required or desired therapeutic response, or in other words, the amount which is sufficient to elicit an appreciable biological response when administered to a patient.

The tablets of the invention can assume any shape or form known in the art of pharmaceutical sciences. The device of the invention can be a pill, sphere, tablet, bar, plate, paraboloid of revolution, ellipsoid of revolution or other known shapes for solid formulations. The tablets can also include surface markings, cuttings, grooves, letters and/or numerals for the purposes of decoration, identification and/or other purposes.

The tablets of the invention can be prepared according to the methods disclosed herein or those well known in the art, more specifically according to the methods disclosed in the disclosure incorporated herein by reference. For example, according to one manufacturing technique, diltiazem and excipients that comprise the core are mixed in solid, semi-solid or gelatinous form, then moistened and sieved through a specified screen to obtain uncoated cores. The uncoated cores are then dried in a dryer and compressed, for example, by punching. The compressed and uncoated cores are then covered with a semipermeable membrane. Subsequently, the semipermeable membrane surrounding the core should be perforated with, for example, laser equipment. Finally, an external coat containing the ACE inhibitor is applied to the semipermeable membrane.

The external coat can be applied as a compression coating, but it is preferably applied as a sprayed coating. The sprayed coating is thinner and lighter than the compression coating, and an osmotic device including the sprayed on external coating is, therefore, smaller than a similar osmotic device having a compression coat. A smaller size osmotic device generally results in increased patient compliance in taking the osmotic device and is therefore advantageous.

The osmotic device can also include a water soluble coat between the semipermeable membrane and the external coat containing ACE inhibitor or diuretic. When a rapidly dissolving or water soluble coat is used in the tablet formulations of the invention, the coat will generally comprise an inert and non-toxic material that is at least partially, and preferably substantially completely, soluble or erodible in an environment of use. The rapidly dissolving coat will be soluble in the buccal cavity and/or upper GI tract, such as the stomach, duodenum, jejunum or upper small intestines. Exemplary materials are disclosed in U.S. Pat. Nos. 4,576,604 and 4,673,405, and the text Pharmaceutical Dosage Forms: Tablets Volume I, Second Edition. A. Lieberman. ed. 1989, Marcel Dekker, Inc. the relevant disclosures of which are hereby incorporated by reference. In preferred embodiments, the rapidly dissolving coat will be soluble in saliva, gastric juices, or acidic fluids.

Materials which are suitable for making the water soluble coat or layer include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. The water soluble coating can comprise other pharmaceutical excipients that do or do not alter the way in which the water soluble coating behaves. The artisan of ordinary skill will recognize that the above-noted materials include film forming polymers.

The inert water soluble coat covering the semipermeable wall and blocking the passageway is made of synthetic or natural material which, through selective dissolution or erosion shall allow the passageway to be unblocked thus allowing the process of osmotic delivery to start. This slow or fast dissolving water soluble coat can be impermeable to a first external fluid, while being soluble in a second external fluid. This property can help to achieve a controlled and selective release of the active compound in the nucleus.

The osmotic device of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

Generally, the terms "tablet" and "osmotic device" are used interchangeably herein in describing the invention. The osmotic device of the invention comprises at least one passageway (pore, hole, or aperture) that communicates the exterior of the semipermeable wall with the core of the device. The passageway can be formed according to any of the known methods of forming passageways in a semipermeable membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., and U.S. Pat. No. 3,845,770 to Theeuwes et al., the disclosures of which are hereby incorporated by reference.

The preformed passageway, e.g., one made by mechanical means, is formed after the semipermeable membrane is applied to the core. It can be formed either before or after the inert water soluble coat and/or drug-containing external coat is applied to the semipermeable membrane.

The advantages of the present system over known systems for administering diltiazem in combination with an ACE inhibitor is improved therapeutic benefit, simplified manufacturing, and increased patient compliance.

ACE inhibitors, diuretics and diltiazem have associated side effects when administered to mammals for the treatment of hypertension. By administering the drugs according to the invention in a chronotherapeutic manner, the mammal receiving these drugs experiences less side effects since the mammal sleeps through the initial onset of the side effects. Literature suggests that diltiazem prolongs the time-to-sleep time, meaning that it takes longer for a mammal to fall asleep if the mammal has been administered diltiazem. By administering the diltiazem according to the invention, diltiazem's negative impact on sleep behavior is reduced, since the onset of this side effect occurs after the mammal has already fallen asleep if the mammal has taken the chronotherapeutic osmotic device a short period of time (less than three hours) before bedtime.

The chronotherapeutic osmotic device of the invention is useful in treating hypertension and related disorders. The chronotherapeutic device can be administered at any time of day for such use; however, its delayed release profile makes the device particularly suitable for administration prior to a rest period, such as bedtime. According to one embodiment, the method of treating hypertension in a mammal comprises the step of administering a chronotherapeutic osmotic device. Another embodiment of the method comprises the step of administering a chronotherapeutic osmotic device comprising: a core comprising diltiazem, an osmagent and one or more excipients; a semipermeable membrane surrounding the core; one or more passageways in the semipermeable membrane; and an immediate release coat surrounding the semipermeable membrane and comprising an ACE inhibitor or diuretic; wherein the device provides a delayed and controlled release of diltiazem and a delayed and rapid release of the ACE inhibitor or diuretic. In some embodiments, the initial delay periods for beginning release of the diltiazem and the ACE inhibitor or diuretic are approximately the same. In other embodiments, the initial delay period for beginning release of the diltiazem is longer than the initial delay period for beginning release of the ACE inhibitor or diuretic. Other embodiments include those wherein the delay period for the ACE inhibitor or diuretic is about 1.5 to 2.5 hours and the delay period for the diltiazem is about 1.5 to 3 hours.

The chronotherapeutic osmotic device of the invention is also useful in treating atherosclerosis and hypercholesterolemia. By coadministration of the diltiazem and an ACE inhibitor, such as enalapril, a significant hypocholesterolemic effect is observed, i.e, the combined administration of the two drugs reduces cholesterol plasma levels in mammals. Such a corbined formulation also impedes the development of atheromatous plaque. Accordingly, the present chronotherapeutic device comprising diltiazem and an ACE inhibitor, such as enalapril, is useful in treating cholesterol related disorders and atherosclerosis.

The invention also provides a method of reducing the observed side effects typically associated with diltiazem and ACE inhibitor or diuretic therapy. The method requires the administration of the drug-containing dosage form within about three hours before bedtime such that the onset of sleep disturbing or discomforting side effects occurs after the mammal has fallen asleep.

The following examples should not be considered exhaustive, but merely illustrative of only a few of the many embodiments contemplated by the present invention. The methods described herein can be followed to prepare osmotic devices according to the invention.

EXAMPLE 1

A large scale batch of osmotic device tablets containing diltiazem hydrochloride (180 mg) and enalapril maleate (5 mg) was prepared by mixing 180.00 g of diltiazem HCl, 134.70 g of anhydrous dextrose and 6.0 g of povidone K90. The mixture was wetting with a blend of 90.00 ml of alcohol 96°, 7.20 g of povidone K90 and 4.50 g of poly (ethylene glycol) 400. The blend was granulated and dried at 40–50° C. for 2 hours; then, it was screened and mixed with 1.50 g of colloidal silicon dioxide. The blend was mixed to homogeneity and 3.60 g of magnesium stearate was added as lubricant. The final blend was tabletting using biconcaves, 9.25-mm diameter punches. Average core weight: 337.5 mg. Hardness from 6 to 12 kp.

A first composition to cover the tablets was prepared as follows: 33.08 g of cellulose acetate and 1.74 g of poly (ethylene glycol) 400 in a mixture of methylene chloride-methyl alcohol 70:30 v/v (volume/volume). This polymer mixture was sprayed onto the tablets in a conventional pan coater to obtain film-coated tablets which membrane coating weighed 34.8 mg approximately. A 0.50-mm hole was drilled through the coating in one face of the tablet.

The second coating was prepared by mixing 2.93 g of copolyvidone, 2.63 g of titanium dioxide, 9.43 g of talc and 5.63 mg of Aluminum Lake Brilliant Blue in isopropyl alcohol. This polymer mixture was sprayed onto the tablets in a conventional pan coater to obtain film-coated tablets which membrane coating weighed 15 mg approximately.

The third coating was prepared by mixing 5.00 g of enalapril maleate, 17.40 g of copolyvidone, 2.60 g of poly (ethylene glycol) 400, 4.70 g of crospovidone, 5.00 g of talc and 0.30 g of colloidal silicon dioxide in isopropyl alcohol. This polymer mixture was sprayed onto the tablets in a conventional pan coater to obtain film-coated tablets which membrane coating weighed 35 mg approximately.

The delayed release external coating was prepared by mixing 31.28 g of methacrylic acid copolymer USP Type A, 2.08 g of poly (ethylene glycol) 6000, 6.60 g of titanium dioxide and 10.04 g of talc in 1110 ml of isopropyl alcohol. This polymer mixture was sprayed onto the tablets in a conventional pan coater to obtain film-coated tablets which membrane coating weighed 25 mg approximately.

Tablets made according to the above procedure had the following ingredients in the approximate amounts indicated:

| Ingredient | Amount |
| --- | --- |
| Core | 277.6–347.6 mg |
| DTZ salt | 162–198 mg |
| Anhydrous Dextrose (Filler) | 100–120 mg |
| PEG 400 (Plasticizer) | 2.6–5.5 mg |
| Povidone K-90 (Binder) | 11.5–16.5 mg |
| Colloidal silicon dioxide (Glidant) | 0.5–3.0 mg |
| Magnesium Stearate (Lubricant) | 1.0–4.6 mg |
| Semipermeable Membrane | 25.5–43.5 mg |
| Cellulose Acetate (Cellulose Ester) | 25–40 mg |
| Polyethylene Glycol 400 (Plasticizer) | 0.5–3.5 mg |
| Inert water soluble coat | 9.01–25.01 mg |
| Copolyvidone (Water soluble polymer) | 2–5 mg |
| Talc (Filler, disintegrant) | 5–15 mg |
| TiO$_2$ (Opaquant) | 2–5 mg |
| Colorant | 0.01–0.1 mg |
| Drug-Containing coat | 22.1–45 mg |
| Enalapril salt (ACE inhibitor) | 4.5–5.5 mg |
| Copolyvidone (water soluble polymer) | 10–20 mg |
| PEG-400 (Plasticizer) | 1.5–5 mg |
| Crospovidone (Disintegrant) | 3–6 mg |
| Talc (Filler) | 3–8 mg |
| Colloidal silicon dioxide (Glidant) | 0.1–5 mg |
| Delayed Release coat | 35–59 mg |
| Methacrylic acid copolymer (Enteric polymer) | 25–33 mg |
| PEG-6000 (Plasticizer) | 1–3 mg |
| TiO$_2$ (Opaquant) | 4–8 mg |
| Talc (Filler) | 5–15 mg |

EXAMPLE 2

The following procedure was used to determine the pharmacokinetic parameters of the chronotherapeutic osmotic devices of the invention and of the commercial products. A single dose open study was carried out in eighteen healthy subjects (non-smoking and within the ages of 21–50). The volunteers received the respective dosage form after an approximately 12 hour fasting period. Following administration, blood samples were drawn periodically from 0–36 hours. Plasma aliquots were obtained immediately and stored at −20° C. They were later analyzed by HPLC (UV detection at 240 nm) to quantify the level of drug present in the sample. The least squares means of the pharmacokinetic parameters detailed above were calculated from the plasma concentration data (time curve). $AUC_{0-t}$ indicates area under the curve from 0–48 hours after administration. $AUC_{0-inf}$ indicates the $AUC_{0-t}$ extrapolated to infinity. $C_{max}$ indicates the maximum plasma concentration of the drug. $T_{max}$ indicates the time to reach $C_{max}$ as measured from initial administration of the dosage form. $K_e$ indicates the elimination rate constant. $T_{1/2}$ indicates the elimination half-life.

EXAMPLE 3

The following tablets were made according to the general procedure described in Example 1 except that no drug-containing external coating was prepared. These tablets had the following general formulation. A drug-containing external coat, an inert water soluble coat and a delayed release coat could be added according to the procedure of Example 1.

|  | Strength Tablets | |
| --- | --- | --- |
|  | 180 mg DTZ | 240 mg DTZ |
| CORE | | |
| DTZ-HCl | 180 mg | 240 mg |
| Anhydrous Dextrose | 134.7 mg | 179.6 mg |
| Colloidal silicon dioxide | 0.6 mg | 0.8 mg |
| PEG 400 | 4.5 mg | 6 mg |
| Povidone K-90 | 13.2 mg | 17.6 mg |
| Colloidal silicon dioxide | 0.9 mg | 1.2 mg |
| Magnesium Stearate | 3.6 mg | 4.8 mg |
| Semipermeable coat | | |
| Cellulose Acetate 101 | 30.32 mg | 31.74 mg |
| Cellulose Acetate 102 | 2.76 mg | 2.89 mg |
| Polyethylene Glycol 400 | 1.74 mg | 1.82 mg |
| Finish coat | | |
| HPMC | 9.04 mg | 12.05 mg |
| PEG 6000 | 2.58 mg | 3.44 mg |
| $TiO_2$ | 3.38 mg | 4.51 mg |

We claim:

1. A chronotherapeutic osmotic device comprising:
   a) a core comprising a therapeutically effective amount of diltiazem (DZ) and at least one osmotic agent or osmopolymer, wherein the core provides a controlled release of diltiazem;
   b) a semipermeable membrane surrounding the core and having a passageway there through; and
   c) an external coat comprising a therapeutically effective amount of an angiotensin converting enzyme (ACE) inhibitor or diuretic, wherein the external coat provides a rapid release of the ACE inhibitor or diuretic; wherein,
   d) at least 70% of the DZ is released in a controlled manner within 20 hours, and at least about 45% of the ACE inhibitor is released within 180 minutes or at least about 75% of the diuretic is released within about 180 minutes after exposure of the osmotic device to an aqueous environment; and
   e) initial release of the DZ and, optionally, ACE inhibitor or diuretic is delayed for a period of at least about 1.5 hour after exposure of the osmotic device to an aqueous environment.

2. The chronotherapeutic osmotic device of claim 1, wherein the external coat is sprayed onto the semipermeable membrane during manufacture of the device.

3. The chronotherapeutic osmotic device of claim 1, wherein the device has a diltiazem release profile approximating the following:

| Time (h) | Released (%) |
| --- | --- |
| 0 | 0 |
| 2 | ≦5 ± 5 |
| 3 | ≦10 ± 5 |
| 5 | 15 ± 5 |
| 7 | 30 ± 5 |
| 8 | 40 ± 5 |
| 11 | 55 ± 5 |
| 14 | 65 ± 5 |
| 17 | 75 ± 10 |
| 21 | 80 ± 10 |
| 24 | ≧80 |

4. The chronotherapeutic osmotic device of claim 1, wherein the device has a diltiazem release profile approximating the following:

| Time (h) | Released (%) |
| --- | --- |
| 0 | 0 |
| 1 | ≦5 ± 5 |
| 3 | 20 ± 5 |
| 5 | 32 ± 5 |
| 7 | 45 ± 5 |
| 9 | 55 ± 5 |
| 11 | 65 ± 5 |
| 13 | 70 ± 5 |
| 15 | 75 ± 8 |
| 19 | 75 ± 10 |
| 24 | ≧75 |

5. The chronotherapeutic osmotic device of claim 3 or 4, wherein the device has an ACE inhibitor or diuretic release profile approximating the following:

| Time (min) | Released (%) |
| --- | --- |
| 0 | 0 |
| 60 | ≦5 |
| 120 | 5 ± 5 |
| 150 | >80 |

6. The chronotherapeutic osmotic device of claim 1, wherein initial release of the ACE inhibitor or diuretic is delayed for a period of about 1.5 to 2.5 hours and initial release of the DZ is delayed for a period of about 1.5 to 3.0 hours after exposure of the device to an aqueous environment.

7. The chronotherapeutic osmotic device of claim 6, wherein the release of DZ begins after release of the ACE inhibitor or diuretic has begun.

8. The chronotherapeutic osmotic device of claim 6, wherein, once release of the ACE inhibitor or diuretic begins, at least about 45% of its ACE inhibitor, or at least 75% of its diuretic, will be released within about 40 minutes.

9. The chronotherapeutic osmotic device of claim 1, wherein the osmotic device delivers the ACE inhibitor or diuretic to the upper GI tract and the majority of diltiazem to the middle to lower GI tract of a mammal to whom the device is administered orally.

10. The chronotherapeutic osmotic device of claim 1, wherein the device provides therapeutically effective amounts of diltiazem for a period of not less than 18 hours and not more than 30 hours after administration of a single device to a mammal.

11. The chronotherapeutic osmotic device of claim 10, wherein the device provides therapeutically effective amounts of diltiazem for a period of not less than 20 hours and not more than 28 hours after administration of a single device to a mammal.

12. The chronotherapeutic osmotic device of claim 1, wherein the device provides a single dose plasma concentration profile for diltiazem approximating the following when administered to a mammal:

| Time after Administration (H) | Mean Plasma Level (ng/ml) | STD (ng/ml) |
| --- | --- | --- |
| 0 | 0.0 | 0.0 |
| 1 | 0.0 | 0.0 |
| 2 | 1.6 | 2.1 |
| 3 | 13.5 | 8.7 |
| 5 | 39.8 | 19.1 |
| 7 | 63.8 | 29.3 |
| 9 | 67.2 | 25.2 |
| 11 | 62.4 | 25.4 |
| 12 | 61.5 | 28.4 |
| 13 | 68.0 | 25.7 |
| 14 | 70.0 | 25.8 |
| 16 | 59.1 | 18.9 |
| 18 | 48.8 | 20.2 |
| 20 | 43.4 | 15.5 |
| 24 | 36.5 | 14.0 |
| 28 | 31.7 | 11.6 |
| 32 | 21.4 | 10.7 |
| 36 | 11.4 | 5.7 |

13. The chronotherapeutic osmotic device of claim 12, wherein the device provides the following approximate pharmacokinetic parameters when administered to a mammal:

| Parameter | Mean | Std Error |
| --- | --- | --- |
| $AUC_{0-t}$ (ng·h/ml) | 1419 | 465.1 |
| $AUC_{0-inf}$ (ng·h/ml) | 1548 | 507.8 |
| $K_e$ (h-1) | 0.1168 | 0.0096 |
| $C_{max}$ (ng/ml) | 81.7 | 25.7 |
| $t_{max}$ (h) | 11.5 | 2.9 |
| $T_{½}$ (h) | 7.7 | 4.3 |

14. The chronotherapeutic osmotic device of claim 1, wherein the device provides a single dose plasma concentration profile for diltiazem approximating the following when administered to a mammal:

| Time after Administration (H) | Mean Plasma Level (ng/ml) | STD (ng/ml) |
| --- | --- | --- |
| 0 | 0.0 | 0.0 |
| 0.5 | 0.1 | 0.4 |
| 1 | 1.9 | 2.5 |
| 2 | 15.8 | 9.9 |
| 4 | 47.6 | 22.6 |
| 6 | 75.7 | 34.7 |
| 8 | 81.7 | 30.0 |
| 10 | 75.6 | 30.5 |
| 12 | 74.6 | 33.9 |
| 13 | 80.9 | 31.7 |
| 14 | 80.8 | 29.1 |
| 16 | 71.4 | 22.5 |
| 18 | 58.1 | 22.4 |
| 20 | 50.2 | 18.0 |
| 24 | 43.8 | 15.9 |
| 28 | 37.5 | 13.7 |
| 32 | 25.9 | 12.7 |
| 36 | 13.8 | 7.3 |

15. The chronotherapeutic osmotic device of claim 14, wherein the device provides the following approximate pharmacokinetic parameters when administered to a mammal:

| Parameter | Mean | Std Error | CV % |
| --- | --- | --- | --- |
| $AUC_{0-t}$ (ng.h/ml) | 1726.3 | 54.8 | 3.2 |
| $AUC_{0-inf}$ (ng.h/ml) | 1867.6 | 60.9 | 3.3 |
| $K_e$ (h-1) | 0.1212 | 0.0096 | 7.9 |
| $C_{max}$ (ng/ml) | 95.2 | 4.1 | 4.3 |
| $t_{max}$ (h) | 10.4 | 0.8 | 7.8 |
| $T_{1/2}$ (h) | 6.97 | 0.48 | 6.8 |

16. The chronotherapeutic osmotic device of claim 1 further comprising an inert water soluble or erodible coat between the semipermeable membrane and the external coat.

17. The chronotherapeutic osmotic device of claim 16 further comprising a finish coat exterior to the external coat.

18. The chronotherapeutic osmotic device of claim 1, wherein the device comprises DZ and the ACE inhibitor enalapril.

19. The chronotherapeutic osmotic device of claim 1, wherein the ACE inhibitor is selected from the group consisting of enalapril (ENA), captopril (CAP), lisinopril (LIS), benazepril (BEN), enalaprilat (ENAP), espirapril (ESP), fosinopril (FOS), moexipril (MXP), quinapril (QNA), ramipril (RAM), perindopril, and trandolapril.

20. The chronotherapeutic osmotic device of claim 1, wherein the diuretic is selected from the group consisting of high-ceiling diuretics, furosemide, bumetanide, ethacrynic acid, torsemide, muzolimide, azosemide, piretanide, tripamide, chlorothiazide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide and benzothiazide.

21. The chronotherapeutic osmotic device of claim 1 further comprising a delayed release coat disposed external to the external coat.

22. The chronotherapeutic osmotic device of claim 1, wherein the external coat comprises a delayed release pharmaceutical excipient and the external coat delays the release of diltiazem from the core of the device.

23. The chronotherapeutic osmotic device of claim 1, wherein the core comprises diltiazem, an osmagent and a pharmaceutical excipient.

24. The chronotherapeutic osmotic device of claim 23, wherein the external coat comprises a pharmaceutical excipient and ACE inhibitor or diuretic.

25. A method of treating hypertension in a mammal, the method comprising the step of administering to the mammal a chronotherapeutic osmotic device according to any one of claims 1–4 or 6–24.

26. A method according to claim 25, wherein the chronotherapeutic osmotic device is administered within three hours prior to a period of sleep.

27. A method of treating hypertension in a mammal comprising the step of administering a chronotherapeutic osmotic device that provides a delayed and rapid release of an ACE inhibitor or a diuretic and a delayed and controlled release of diltiazem.

28. A method according to claim 27, wherein the chronotherapeutic osmotic device comprises:
   a) a core comprising diltiazem, an osmagent and one or more excipients;
   b) a semipermeable membrane surrounding the core;
   c) one or more passageways in the semipermeable membrane;
   d) an immediate release coat surrounding the semipermeable membrane and comprising an ACE inhibitor or diuretic; and
   e) a delayed release coat surrounding the immediate release coat.

29. A method according to claim 28, wherein the initial delay periods for beginning release of the diltiazem and the ACE inhibitor or diuretic are approximately the same.

30. A method according to claim 28, wherein the initial delay period for beginning release of the diltiazem is longer than the initial delay period for beginning release of the ACE inhibitor or diuretic.

31. A method according to claim 28, wherein the delay period for the ACE inhibitor or diuretic is about 1.5 to 2.5 hours and the delay period for the diltiazem is about 1.5 to 3 hours.

32. A method according to claim 31, wherein at least 45% of the ACE inhibitor is released within about 40 minutes after completion of the delay period or at least 75% of the diuretic is released within about 40 minutes after completion of the delay period.

33. A method according to claim 28, wherein the osmotic device further comprises an inert water soluble or erodible coat between the semipermeable membrane and the immediate release coat.

34. A method according to claim 28, wherein the chronotherapeutic osmotic device is administered within three hours prior to a period of sleep.

35. A method according to claim 28, wherein the ACE inhibitor is selected from the group consisting of enalapril (ENA), captopril (CAP), lisinopril (LIS), benazepril (BEN), enalaprilat (ENAP), espirapril (ESP), fosinopril (FOS), moexipril (MXP), quinapril (QNA), ramipril (RAM), perindopril, and trandolapril.

36. A method according to claim 28, wherein the diuretic is selected from the group consisting of high-ceiling diuretics, furosemide, bumetanide, ethacrynic acid, torsemide, muzolimide, azosemide, piretanide, tripamide, chlorothiazide, hydrochlorothiazide, chlorthalidone, idapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide and benzothiazide.

37. A chronotherapeutic osmotic device comprising:
   a) a core comprising diltiazem, an osmagent and one or more excipients;
   b) a semipermeable membrane surrounding the core;
   c) one or more passageways in the semipermeable membrane;
   d) an immediate release coat surrounding the semipermeable membrane and comprising an ACE inhibitor or diuretic; and
   e) a delayed release coat surrounding the immediate release coat.

38. A chronotherapeutic osmotic device according to claim 37, wherein the initial delay periods for beginning release of the diltiazem and the ACE inhibitor or diuretic are approximately the same.

39. A chronotherapeutic osmotic device according to claim 37, wherein the initial delay period for beginning release of the diltiazem is longer than the initial delay period for beginning release of the ACE inhibitor or diuretic.

40. A chronotherapeutic osmotic device according to claim 37, wherein the delay period for the ACE inhibitor or diuretic is about 1.5 to 2.5 hours and the delay period for the diltiazem is about 1.5 to 3 hours.

41. A chronotherapeutic osmotic device according to claim 40, wherein at least 75% of the ACE inhibitor is released within about 40 minutes after completion of the delay period or at least 75% of the diuretic is released within about 40 minutes after completion of the delay period.

42. A chronotherapeutic osmotic device according to claim 37, wherein the osmotic device further comprises an inert water soluble or erodible coat between the semipermeable membrane and the immediate release coat.

43. A chronotherapeutic osmotic device according to claim 37, wherein the chronotherapeutic osmotic device is administered within three hours prior to a period of sleep.

44. A chronotherapeutic osmotic device according to claim 37, wherein the ACE inhibitor is selected from the group consisting of enalapril (ENA), captopril (CAP), lisinopril (LIS), benazepril (BEN), enalaprilat (ENAP), espirapril (ESP), fosinopril (FOS), moexipril (MXP), quinapril (QNA), ramipril (RAM), perindopril and trandolapril.

45. A chronotherapeutic osmotic device according to claim 37, wherein the diuretic is selected from the group consisting of high-ceiling diuretics, furosemide, bumetanide, ethacrynic acid, torsemide, muzolimide, azosemide, piretanide, tripamide, chlorothiazide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, and benzothiazide.

46. A chronotherapeutic osmotic device according to any one of claims 1, 3, or, 12, 13, or 37 wherein the osmotic device comprises the following ingredients in the approximate amounts indicated:

| Ingredient | Amount |
|---|---|
| Core | 277.6–347.6 mg |
| DTZ salt | 162–198 mg |
| Filler | 100–120 mg |
| Plasticizer | 2.6–5.5 mg |
| Binder | 11.5–16.5 mg |
| Semipermeable Membrane | 25.5–43.5 mg |
| Cellulose Ester | 25–40 mg |
| Plasticizer | 0.5–3.5 mg |
| Inert water soluble coat (optional) | 9.01–25.01 mg |
| Water soluble polymer | 2–5 mg |
| Filler | 5–15 mg |
| Opaquant | 2–5 mg |
| Drug-Containing coat | 22.1–45 mg |
| ACE inhibitor | 4.5–5.5 mg |
| water soluble polymer | 10–20 mg |
| Plasticizer | 1.5–5 mg |
| Disintegrant | 3–6 mg |
| Filler | 3–8 mg |
| Delayed Release coat | 35–59 mg |
| Enteric polymer | 25–33 mg |
| Plasticizer | 1–3 mg |
| Opaquant | 4–8 mg |
| Filler | 5–15 mg |

47. A chronotherapeutic controlled release dosage form comprising:
   a) a therapeutically effective amount of diltiazem;
   b) a therapeutically effective amount of an ACE inhibitor or diuretic; and
   c) a delayed release composition;
   wherein the dosage form releases the diltiazem and the ACE inhibitor or diuretic agent after an initial delay period, after which the diltiazem is released at a controlled rate and the ACE inhibitor or diuretic is released rapidly.

48. The dosage form of claim 47 comprising:
   a. a different second composition comprising a therapeutically effective amount of the ACE inhibitor or diuretic.

49. The dosage form of claim 48, wherein the delayed release composition surrounds at least one of the first and second compositions.

50. The dosage form of claim 49, wherein the second composition surrounds the first composition, and the delayed release composition surrounds the second composition.

51. The dosage form of claim 48, wherein the delayed release composition is included within at least one of the first and second compositions.

52. The dosage form of claim 51, wherein the delayed release composition is included within the second composition, and the second composition surrounds the first composition.

53. The dosage form of claim 48, wherein the delay period for initial release of the diltiazem is approximately the same as the delay period for initial release of the ACE inhibitor or diuretic.

54. The dosage form of claim 48, wherein the delay period for initial release of the diltiazem is different than the delay period for initial release of the ACE inhibitor or diuretic.

55. The dosage form of claim 48, wherein the delay period for initial release of the diltiazem is about 1.5 to 3 hours, and the delay period for initial release of the ACE inhibitor or diuretic is about 1.5 to 2.5 hours.

56. The dosage form of claim 48, wherein the ACE inhibitor is selected from the group consisting of enalapril (ENA), captopril (CAP), lisinopril (LIS), benazepril (BEN), enalaprilat (ENAP), espirapril (ESP), fosinopril (FOS), moexipril (MXP), quinapril (QNA), ramipril (RAM), perindopril, and trandolapril.

57. The dosage form of claim 48, wherein the diuretic is selected from the group consisting of high-ceiling diuretics, furosemide, bumetanide, ethacrynic acid, torsemide, muzolimide, azosemide, piretanide, tripamide, chlorothiazide, hydrochlorothiazide, chlorthalidone, indipamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide and benzothiazide.

58. The dosage form of claim 51, wherein the delayed release composition is included within the first composition, and the second composition surrounds the first composition.

59. A chronotherapeutic osmotic device according to claim 5 wherein the osmotic device comprises the following ingredients in the approximate amounts indicated:

| Ingredient | Amount |
|---|---|
| Core | 277.6–347.6 mg |
| DTZ salt | 162–198 mg |
| Filler | 100–120 mg |
| Plasticizer | 2.6–5.5 mg |
| Binder | 11.5–16.5 mg |
| Semipermeable Membrane | 25.5–43.5 mg |
| Cellulose Ester | 25–40 mg |
| Plasticizer | 0.5–3.5 mg |
| Inert water soluble coat (optional) | 9.01–25.01 mg |
| Water soluble polymer | 2–5 mg |
| Filler | 5–15 mg |
| Opaquant | 2–5 mg |
| Drug-Containing coat | 22.1–45 mg |
| ACE inhibitor | 4.5–5.5 mg |
| water soluble polymer | 10–20 mg |
| Plasticizer | 1.5–5 mg |
| Disintegrant | 3–6 mg |
| Filler | 3–8 mg |
| Delayed Release coat | 35–59 mg |
| Enteric polymer | 25–33 mg |
| Plasticizer | 1–3 mg |
| Opaquant | 4–8 mg |
| Filler | 5–15 mg |

\* \* \* \* \*